(12) United States Patent
Wheeler

(10) Patent No.: US 7,761,463 B2
(45) Date of Patent: Jul. 20, 2010

(54) SELF-SERVE PATIENT CHECK-IN AND PREVENTIVE SERVICES KIOSK

(75) Inventor: Gary A. Wheeler, Fort Irwin, CA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 545 days.

(21) Appl. No.: 11/133,361

(22) Filed: May 20, 2005

(65) Prior Publication Data

US 2005/0261942 A1    Nov. 24, 2005

Related U.S. Application Data

(60) Provisional application No. 60/572,480, filed on May 20, 2004.

(51) Int. Cl.
*G06F 17/30* (2006.01)
(52) U.S. Cl. .............. 707/769; 707/783; 707/E17.014; 705/2; 705/3
(58) Field of Classification Search .............. 707/3, 707/10, 101, 104.1, 999.01, 999.107, 999.003, 707/769, 783, E17.014; 705/2, 3
See application file for complete search history.

(56) References Cited

U.S. PATENT DOCUMENTS

| | | | |
|---|---|---|---|
| 4,839,822 A | 6/1989 | Dormond et al. | |
| 4,945,476 A | 7/1990 | Bodick et al. | |
| 5,809,476 A | 9/1998 | Ryan | |
| 5,845,256 A * | 12/1998 | Pescitelli et al. | 705/4 |
| 5,924,074 A | 7/1999 | Evans | |
| 5,964,700 A | 10/1999 | Tallman et al. | |
| 5,970,466 A | 10/1999 | Detjen et al. | |
| 5,974,389 A | 10/1999 | Clark et al. | |
| 6,047,259 A | 4/2000 | Campbell et al. | |
| 6,055,506 A | 4/2000 | Frasca, Jr. | |
| 6,119,096 A | 9/2000 | Mann et al. | |
| 6,206,829 B1 | 3/2001 | Iliff | |
| 6,581,038 B1 | 6/2003 | Mahran | |
| 6,684,188 B1 | 1/2004 | Mitchell et al. | |
| 6,808,112 B2 | 10/2004 | Jacobi et al. | |
| 6,876,780 B1 | 4/2005 | Nielsen et al. | |

(Continued)

FOREIGN PATENT DOCUMENTS

WO    WO 00/45301    8/2000

(Continued)

OTHER PUBLICATIONS

Vecna, Inc., "Patent Kiosk Applications Development and Support, Technical Proposal", Jun. 14, 2002.

(Continued)

*Primary Examiner*—Leslie Wong
(74) *Attorney, Agent, or Firm*—Elizabeth Arwine

(57) ABSTRACT

A medical check-in and data communication kiosk for efficiently checking-in patients at a medical facility and/or exchanging relevant data with the patient. A patient automatically provides initial identification information by swiping, scanning, etc., an I.D. card and the kiosk then accesses various legacy database systems to gather all relevant medical data corresponding to the particular patient. The patient is requested to verify and/or update any third party payer information, such as insurance information, and is also informed of suggested preventive healthcare actions.

13 Claims, 7 Drawing Sheets

U.S. PATENT DOCUMENTS

| | | | |
|---|---|---|---|
| 7,490,048 B2* | 2/2009 | Joao | 705/3 |
| 2002/0016720 A1 | 2/2002 | Poropatich et al. | |
| 2002/0035493 A1* | 3/2002 | Mozayeny et al. | 705/5 |
| 2002/0035541 A1* | 3/2002 | Makino et al. | 705/43 |
| 2002/0049617 A1* | 4/2002 | Lencki et al. | 705/4 |
| 2002/0055872 A1* | 5/2002 | LaBrie et al. | 705/14 |
| 2002/0156672 A1* | 10/2002 | Burko | 705/9 |
| 2003/0078806 A1 | 4/2003 | Kudryk et al. | |
| 2003/0187688 A1* | 10/2003 | Fey et al. | 705/2 |
| 2004/0030669 A1* | 2/2004 | Harris | 707/1 |
| 2004/0098740 A1* | 5/2004 | Maritzen et al. | 725/27 |
| 2004/0099731 A1* | 5/2004 | Olenick et al. | 235/380 |
| 2004/0107125 A1* | 6/2004 | Guheen et al. | 705/7 |
| 2004/0181454 A1* | 9/2004 | Manno | 705/21 |
| 2004/0186744 A1* | 9/2004 | Lux | 705/2 |
| 2004/0193448 A1* | 9/2004 | Woodbridge et al. | 705/2 |
| 2004/0232219 A1* | 11/2004 | Fowler | 235/380 |
| 2005/0027562 A1* | 2/2005 | Brown | 705/2 |
| 2005/0187948 A1* | 8/2005 | Monitzer et al. | 707/100 |
| 2005/0228692 A1* | 10/2005 | Hodgdon | 705/2 |
| 2007/0118413 A1* | 5/2007 | Javors | 705/4 |
| 2008/0040421 A1 | 2/2008 | VanKoevering | |

OTHER PUBLICATIONS

Vecna, Inc., Response to Solicitation No. A4S21S0237, "Patient Kiosk Application Development and Support", Dec. 21, 2003.

Self-Service & Kiosk Association, http://www.kiosks.org/, printed on Oct. 28, 2009.

Rocky Mountain Multimedia, http://www.rockmedia.com/, printed on Oct. 28, 2009.

Friendlyway, Touch Screen Kiosks, http://www.friendlyway.com/touch-screen-kiosks/kiosk-design-butler/, printed on Oct. 28, 2009.

Elo TouchSystems, http://elotouch.com/, printed on Oct. 28, 2009.

File history for trademark registration 3,122,176 (U.S. Appl. No. 78698557) registered on Jul. 25, 2006.

OTech Group LLC, The OTech Check-In Kiosk, http://www.otechgroupllc.com/, printed on Dec. 23, 2009.

DynaTouch Corporation—Healthcare Kiosks, http://www.dynatouch.com/healthcare/healthcare_kiosk.aspx, printed on Dec. 22, 2009.

Friendlyway, Touch screen kiosks, Internet kiosks software, http://www.friendlyway.com/touch-screen-kiosks/overview, printed on Dec. 22, 2009.

File history for trademark registration 2,959,740 (U.S. App. No. 78396868) registered on Jun. 7, 2005.

File history for trademark registration 1,891,638 (U.S. App. No. 74292704) registered on Apr. 25, 1995.

File history for trademark registration 2,785,272 (U.S. App. No. 76030321) registered on Nov. 25, 2003.

* cited by examiner

Demographics

We have as your home address and phone numbers

1234 SOMEWHERE ST

CITY, STATE 12345
Home Phone: 123-456-7890
Work Phone: 333-333-3333

Is this correct?

( YES )  ( NO )

FIG. 4

Supplementary Health Insurance

We have as your supplementary health insurance

No third-party insurance found

Is this correct?

( YES )   ( NO )

FIG. 5

Welcome, John Smith

You have the following appointments scheduled today. Please select the one you are checking in for Dr. Cohen at 0830 in Family Health Clinic. ☑

Dr. Stevenson at 1425 in Dermatology Clinic. ☐

Please press OK and follow screens to check in (OK)

FIG. 6

Health Maintenance

Your health maintenance data is:

| Vitals: | | Due Items: | Overdue Items: |
|---|---|---|---|
| Systolic Blood Pressure | 144 | -Fecal Occult Blood | |
| Diastolic Blood Pressure | 94 | -Sigmoidoscopy | |
| Height | 5'10" | -Colonoscopy | |
| Weight | 128.6 lbs. | Pap Smear | |
| Body Mass Index | | | |

Press OK to continue.

SELF-SERVE PATIENT CHECK-IN AND PREVENTIVE SERVICES KIOSK

CROSS REFERENCE TO RELATED APPLICATIONS

This application is an application filed under 35 U.S.C. §111(a) claiming benefit pursuant to 35 U.S.C. §119(e)(1) of the filing date of the Provisional Application 60/572,480 filed on May 20, 2004 pursuant to 35 U.S.C. §111(b).

FIELD OF THE INVENTION

The present invention relates generally to technology for stream-lining patient check-in procedures and personal patient data updating at a medical facility. In particular, the present invention relates to a method and associated system for efficiently checking-in patients at a healthcare facility and efficiently providing up-to-date information to both the patients as well as any related healthcare records systems.

BACKGROUND OF THE INVENTION

In accordance with conventional healthcare check-in methods and systems, patients desiring a personal consultation with a medical practitioner, either pursuant to a prior appointment or otherwise, are required to wait in a queue before being afforded the opportunity to be personally "checked-in" by a receptionist or other medical facility personnel. In addition to relaying the reason for the visit, the typical check-in process also consists of verification of the patient's demographical information, e.g., name, address, phone number, social security number, etc., and verification of the patient's current medical insurance information or any other third party payer information. Typically, patients must wait their respective turn while other patients complete paperwork or otherwise are occupying the facility personnel. Accordingly, the check-in process can take an extremely long time, depending primarily on the number of other patients waiting to check-in and the speed by which each patient is able to check-in.

Additionally, to obtain information about future appointments, such as date, time and location of the appointment(s), the patient typically has to request that the receptionist provide documentation regarding the appointment information (e.g., hand-writing the appointments on appointment cards). Thus, the conventional medical check-in procedure is not centralized and does not readily provide the patient with efficient access to his or her medical information. The present invention addresses these and other issues with respect to conventional medical facility check-in and data verification systems.

In accordance with certain exemplary embodiments of the invention, described in detail below, various medical databases and legacy systems are interfaced to provide medical data. A brief description of a few exemplary existing databases and systems is provided below. However, it is recognized that various other databases and systems can be interfaced in accordance with the present invention to provide additional access to other data when necessary.

For example, the Composite Health Care System (CHCS) is a DoD Health System that provides ability to appoint patients, order and track results of laboratory and radiology studies, and order and track prescription data. CHCS maintains vast medical records for over four million DoD beneficiaries.

CHCS II is an enterprise level computer-based patient record (CPR) system for the DoD Military Health System. It provides anytime, anywhere delivery of patient records to the point of care. CHCS II combines structured documentation with automated coding compliance.

Additionally, the Integrated Clinical Database (ICDB) technology platform is also a development of the DoD Military Health System (MHS) and supports healthcare delivery. Using web technologies, ICDB leverages existing legacy systems and Internet-based capabilities to deliver real-time, efficient and cost-effective information tailored to the needs of providers and their patients. Along with physician, nurse and technician-focused tools, the ICDB enables the MHS to go beyond episodic care and into the realm of prevention and population health management by helping to identify and target "at-risk" members for early intervention.

Working as a force multiplier for existing clinical information systems, ICDB enables the vision of a seamless, integrated, and worldwide healthcare delivery environment that supports the worldwide operations of the Air Force Medical Service (AFMS) and the MHS. It also provides an easily accessible conduit to the clinical information necessary to improve readiness and support early detection and monitoring of chemical and biological attacks.

These databases, and more, can be accessed in accordance with the present invention to provide efficient and informative data to the patient each time the patient checks-in to a medical facility equipped with a medical kiosk, as described below.

In view of the exemplary databases and systems mentioned above, it should be recognized that the present invention can interface with both civilian and military databases and can be adapted to interface with virtually any compatible database to provide access to needed data.

SUMMARY OF THE INVENTION

Illustrative, non-limiting embodiments of the present invention overcome the aforementioned and other disadvantages associated with conventional medical check-in methods and associated devices.

In view of the aforementioned problems with the conventional approach to medical check-in procedures, one inventive aspect of the present invention lies in providing a patient self-service medical check-in system embodied, for example, in a self-service kiosk that is connected to various databases and other legacy systems. Another inventive aspect of the present invention is the synergy that results from the use of such a medical kiosk in the workflow of patient registration for a medical visit (or encounter) and the verification of information as part of the registration process without requiring the personal assistance of hospital personnel. A self-service check-in procedure and its respective system, especially in the health care field, is believed to be novel.

Although efficient patient check-in is one valuable application for the invention, a skilled artisan would understand that the exchange of data between the patient and external database systems can also be performed without requiring that the patient actually be checked-in to the facility.

More particularly, one embodiment of the invention includes a system for providing efficient access to patient data at a medical facility, the system having a self-service kiosk that has an input device operable to input data from a user, a processor and a display screen for visually providing data to the user, and a server in communication with the processor and operable to store data and selectively access data from at least one external database, wherein relevant data with respect to the patient is downloaded from one or more of the external databases via the server and provided to the user via the kiosk.

A further embodiment of the invention includes a method for efficiently exchanging data with patients at a medical facility, the method including providing one or more individual self-service kiosks operable to interface with the patients via one or more of a visual display and an audible speaker, wherein the kiosks are controlled via a processor. A method consistent with this further embodiment also includes presenting an identification card at one of the kiosks, wherein the identification card uniquely identifies an individual patient, requesting verification of certain personal information from the individual patient and accessing one or more databases to obtain medical data corresponding to the individual patient.

Another embodiment in accordance with the invention includes a self-service medical kiosk that has a display device operable to convey certain data to a patient and also request verification of other data from the patient and a processing device operable to receive data inputted by the patient and communicate with a server, wherein the medical kiosk is operable to access one or more external databases and obtain and display accessed data to the patient on the display device.

Still further, another embodiment of the invention includes a system for efficiently exchanging information with patients at a medical facility, the system having means for interacting with a patient and obtaining personal identification information about the patient, means for connecting the kiosk to one or more database systems external to the medical facility and means for verifying one or more of patient personal demographic information and patient insurance or other payer information.

As used herein "substantially", "generally", and other words of degree, are used as a relative modifier intended to indicate permissible variation from the characteristic so modified. It is not intended to be limited to the absolute value or characteristic which it modifies but rather approaching or approximating such a physical or functional characteristic.

BRIEF DESCRIPTION OF THE DRAWINGS

The object and features of the present invention will become more readily apparent from the following detailed description of the exemplary embodiments taken in conjunction with the accompanying drawings in which:

FIG. 4 is an exemplary screen-shot representative of when the system queries a patient about contact information, in accordance with the present invention.

FIG. 5 is an exemplary screen-shot representative of what the display might look like when the system queries the patient about insurance coverage information, in accordance with the present invention.

FIG. 6 is an exemplary screen-shot representative of what the display might look like when the system informs the patient about scheduled appointments, in accordance with the present invention.

FIG. 7 is an exemplary screen-shot representative of what the display might look like when the system informs the patient about suggested preventive healthcare issues, in accordance with the present invention.

DETAILED DESCRIPTION OF ILLUSTRATIVE, NON-LIMITING EMBODIMENTS

Exemplary, non-limiting, embodiments of the present invention are discussed in detail below. While specific configurations are discussed to provide a clear understanding, it should be understood that the specific embodiments and their respective configurations are provided for illustration purposes only. A person skilled in the relevant art will recognize that other configurations may be used without departing from the spirit and scope of the invention.

Figure 2:
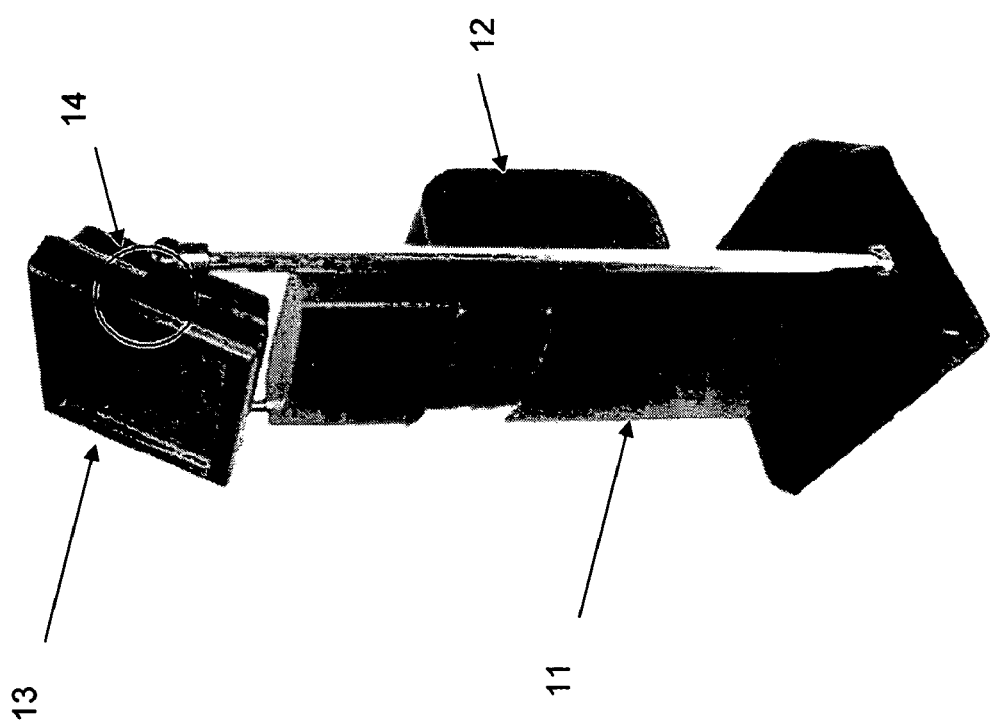
FIG. 2 is an illustration of a single medical check-in kiosk in accordance with the present invention.

One exemplary embodiment of the invention includes a number of self-service patient check-in and medical ailment/disease preventive service medical kiosks. A more detailed view of an exemplary embodiment of a self-service kiosk in accordance with the present invention is illustrated in FIG. 2.

Figure 1:
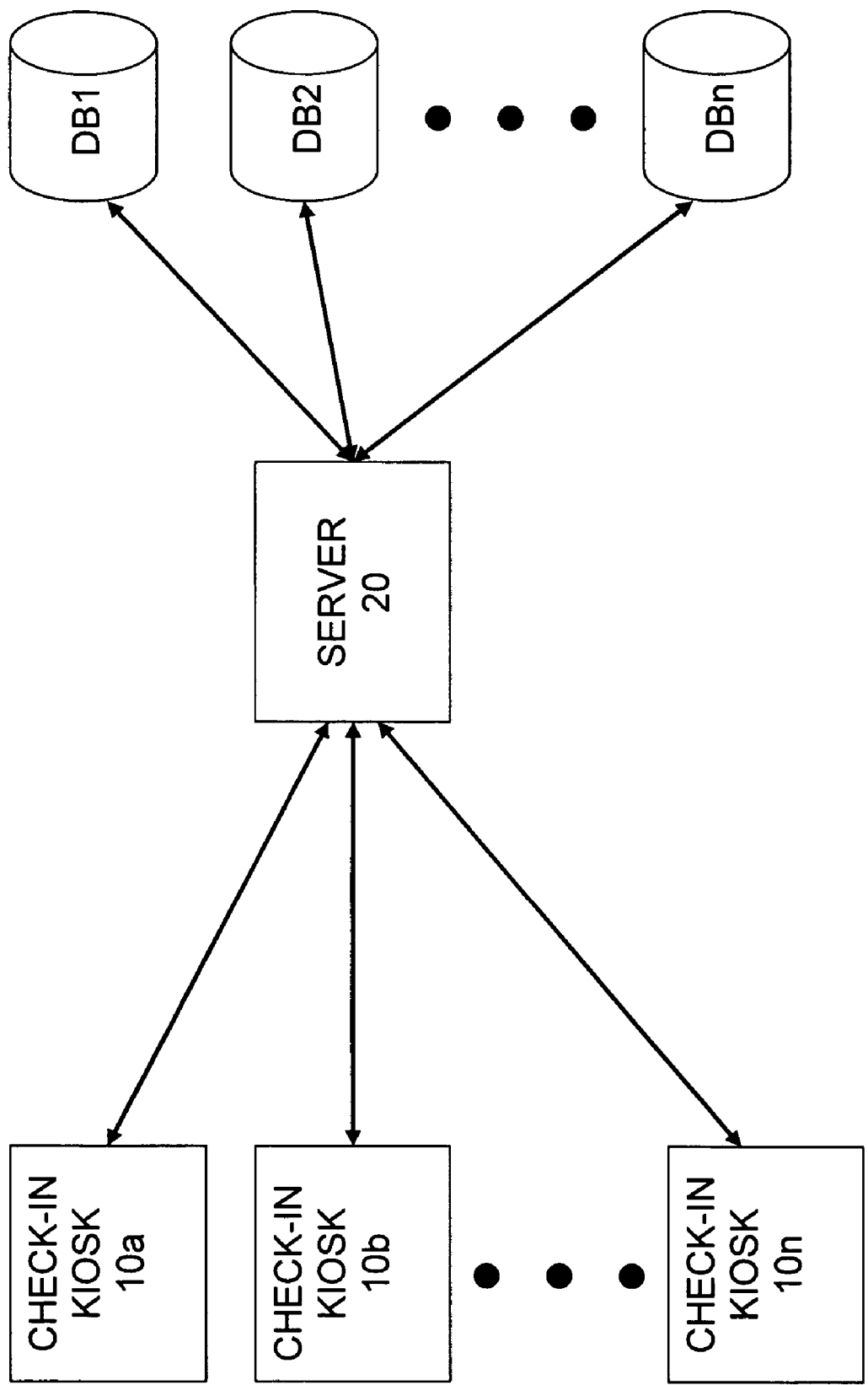
FIG. 1 is a block diagram illustrating a system in accordance with the present invention.

Referring to FIG. 1, in accordance with one embodiment, a system employing a number of individual kiosks is provided. The check-in kiosks, 10a-10n, are each connected in a Local Area network (LAN) configuration with a server 20 which is, in turn, connected via two-way communications links, to various databases (BD1 ... DBn). The LAN can be a wireless LAN (WLAN) or it can use cables to interconnect each device using Ethernet, i.e., in accordance with the IEEE 802.3 standard, or other suitable cabling and data delivery technology. The connection from the server 20 to the legacy database systems, DB1 ... DBn, can be made via a web-based database query system such as Oracle®, which a relational database management system, RDBMS, copyrighted by Oracle Corporation of Redwood Shores, Calif., or any other suitable communication link.

Kiosks 10a-10n are located, for example, in the reception area of a medical facility, such as a hospital, clinic, doctor's office, etc. When a patient (not illustrated) enters a facility that is equipped with a system according to the present invention, the patient is greeted by a number of individual self-service kiosks, each spaced apart from one another in order to afford the patient a certain level of privacy as he or she answers personal questions displayed on the screen. Accordingly, because a number of individual kiosks are provided, the patient is not required to wait in a line in order to inform facility personnel of their arrival.

Figure 3:
FIG. 3 is an exemplary screen-shot representative of what an initial display might look like, in accordance with the present invention.

According to the present embodiment, a patient is instructed, via the display device, to slide or scan his or her personal identification card into the system by using a card reader or scanner provided on each of the kiosks. A sample "screen shot" representative of what the display of the kiosk might look like when the system instructs the patient to scan his or her identification card is illustrated at FIG. 3. Further, according to the present embodiment, the display device is a touch-screen display such that patients can easily touch the appropriate portion of the screen in response to various instructions and/or queries.

The data read from the card uniquely identifies the patient by using a unique alpha-numeric combination or some other type of data that corresponds only to the one individual patient. The data can be stored on the card in a magnetic strip, bar code, or any other suitable format for storing data. Only after the identification of the person corresponding to the data on the card has been established can any personal or medical information with respect to the patient be accessed. Accordingly, to maintain each patient's privacy, personal health information, or otherwise sensitive data corresponding to each patient, is not accessible or displayed at the kiosk display device until the patient's identification is made based on data read from the card.

It should be noted, although the present embodiment includes a card reader for security purposes, it would be clear to one of skill in the art that such security measures may be dispensed with if desired. For example, instead of providing a personal identification card to the system, a patient could be requested to merely enter his or her name or other identifying information on the touch-screen display and the patient's individual medical-related data could be accessed and processed, accordingly.

According to this embodiment, once the patient's identification has been confirmed at the kiosk, certain personal data corresponding to the patient is then verified. For example, the display screen at the kiosk displays various inquiries regarding the patient's contact information, e.g., home and work addresses, phone numbers, e-mail addresses, etc. A sample "screen shot" representative of what the display might look like when the system is querying the patient about contact information is illustrated at FIG. 4. Additionally, relevant data regarding the patient's insurance information can be updated as well. For example, the display device at the kiosk is controlled to query the patient about primary and secondary insurance coverage as well as any other relevant forms of personal or third party payment. A sample "screen shot" representative of what the display might look like when the system is querying the patient about insurance coverage information is illustrated at FIG. 5. The patient is asked to confirm or update all information necessary to facilitate expeditious payment.

As mentioned above, each kiosk, 10a-10n, is connected via bi-directional communications links to various medical records networks, DB1-DBn. For example, in accordance with the present embodiment, each kiosk 10a-10n is linked, via server 20, to various legacy databases, such as CHCS, ICDB and CHCS II. Once the personal data pertaining to the individual patient is recorded and/or updated by a processor at the kiosk, the data is utilized to form a query from the relevant databases. For example, a structured data language (SQL) query can be formed to access data from the CHCS database to obtain the patient's latest medical history, including recent test results, blood pressure, etc.

In accordance with a further aspect of the invention, the system permits patients to retrieve data regarding future pending appointments during the check-in procedure as a reminder to patients. For example, a sample "screen shot" representative of what the display might look like when the system informs the patient about scheduled appointments is illustrated at FIG. 6. In other words, after the system verifies the patient's identity and retrieves the patient's relevant information from the necessary database(s), the patient is reminded about any appointments the patient has scheduled for that day. Additional information such as the name of the doctor or personnel the appointment is with, the location of the appointment, directions to that location, time of the appointment, etc., are displayed.

According to another aspect of the invention, by accessing the patient's medical records via the various databases (DB1-DBn), the system is able to notify the patient if there are any suggested upcoming preventive health measures that should be addressed, such as health screenings, examinations, shots, etc. Additionally, the patient can be informed whether the suggested tests, etc., are upcoming or past due. For example, a sample "screen shot" representative of what the display might look like when the system informs the patient about suggested preventive healthcare issues is illustrated at FIG. 7.

In addition to displaying the suggested preventive healthcare tests, etc., on the kiosk display device, a further aspect of the present invention permits the patient to printout any information that is displayed on paper. An additional embodiment adds a preventive health report card that would provide information regarding, for example, cardiovascular risk (previous blood pressure or recent LDL cholesterol score), women's health (PAP or mammography), cancer screening (e.g., colorectal cancer), immunizations, and obesity (e.g., Body Mass Index based on previous visit statistics).

An alternative embodiment provides an interactive voice response system for reporting laboratory results that are normal/routine.

Once the patient has been checked into the facility system and all relevant data has been verified and/or revised, and the patient has been provided with suggested known preventive measures, the kiosk then notifies the appropriate facility personnel that the patient has checked in and is ready for his or her appointment. For example, the kiosk is equipped with a wireless paging device that automatically pages the nurse or other personnel that the patient is ready for his or her appointment.

As mentioned above, an exemplary embodiment of a medical kiosk 10 in accordance with the present invention is illustrated in FIG. 2. The medical kiosk illustrated in FIG. 2 includes a stand (or housing) 11 holding a computer (or other processing device) 12 that interacts with the healthcare network (including legacy medical databases such as CHCS) via a server 20 (FIG. 1), creates the user interface, prints out documents as requested, and intakes identification information and other user provided information. According to one embodiment, the stand also houses a printer (not illustrated) and supports a monitor 13 that can be a touch-screen or a regular monitor with keyboard or other data entry device connected, and a card reader 14, or other information reader such as a magnetic pad, with each of these components connected to the computer 12 located at the kiosk. The computer executes software to implement the system, as discussed above, and to interact with the patient, medical database(s), and medical staff.

Exemplary advantages of a system in accordance with the present invention include allowing individuals to avoid long check-in lines at medical facilities such as clinics or hospitals, preventing or minimizing inconsistencies in medical insurance information, improving accuracy of medical prescriptions, and improving efficiency by allowing appropriate utilization of nursing staff.

The invention also addresses a variety of metrics that are to be met by medical centers. The system is capable of improving the quality of care by increasing awareness of patients in offered preventive services and issues that need to be discussed/addressed during the visit, improving the efficient operation of patient care by better utilizing nursing staff and increasing the overall breadth of medical issues that may be addressed during a patient encounter, significantly decreasing provider encounter times, decreasing the number of clerks needed to staff the check-in window, thus, freeing the clerks up to do other activities, increasing the number of check-in points available to patients in addition to the check-in window, thus, reducing check-in time by up to ten minutes during peak hours, increasing third party collections because of the improved collection of third party payers including health insurance companies, increasing the participation of the patient in the process and verification of information, and the interface is easily understood by first-time users.

The invention could also be utilized to interact with medical databases. According to a further embodiment, on-line service performance surveys are also provided. For example, the patient returns to the kiosk immediately after attending his or her scheduled appointment and completes a survey querying the patient about various satisfaction levels with respect to the patient's visit. In this manner, the facility is able to collect patient satisfaction data in a simple manner contemporaneously with the patient's visit and the patient does not need to wait in a line in order to obtain the survey questions.

While various aspects of the present invention have been particularly shown and described with reference to the exemplary, non-limiting, embodiments above, it will be understood by those skilled in the art that various additional aspects and embodiments may be contemplated without departing from the spirit and scope of the present invention.

Other aspects, objects and advantages of the present invention can be obtained from a study of the drawings, the disclosure and the appended claims.

What is claimed is:

1. A method for self-service by a patient during a visit to a medical facility, comprising:
   scanning a personal identification card of the patient via at least one kiosk located at the medical facility, said at least one kiosk comprising a card reader, a touch-screen display device, a wireless paging device, and an interactive voice response system;
   after confirming the patient's identification, verifying personal information from the patient via the touch-screen display device and updating the personal information at the at least one kiosk;
   accessing at least one database to obtain medical data corresponding to the patient;
   displaying appointments scheduled for the patient on the touch-screen display device;
   asking the patient to confirm for which appointment the patient is checking in;
   reporting routine laboratory results via an interactive voice response system;
   displaying preventive health measures that are upcoming for the patient on the touch-screen display device;
   displaying preventive health measures that are overdue for the patient on the touch-screen display device; and
   notifying a medical professional that the patient is checked into the facility and ready for an appointment.

2. A method according to claim 1, wherein said accessing at least one database to obtain medical data comprises accessing a military health system.

3. A method according to claim 1, wherein said accessing at least one database to obtain medical data comprises accessing both civilian and military databases.

4. A method according to claim 1, wherein the at least one database provides clinical information to support detection and monitoring of chemical and biological attacks.

5. A method according to claim 1, wherein the upcoming preventive health measures comprise a colonoscopy.

6. A method as claimed in claim 1, comprising verifying health insurance information from the patient.

7. A method according to claim 1, comprising providing the patient with a name of a doctor or personnel an appointment is with, a location of the appointment, directions to the location, and time of the appointment.

8. A method according to claim 1, comprising displaying appointments scheduled on the same day for the patient.

9. A method according to claim 1, further comprising displaying a preventative health report card for the patient comprising information regarding cardiovascular risk and obesity on the touch-screen display device.

10. A method according to claim 9, wherein the preventative health report card comprises cardiovascular risk information comprising previous blood pressure and LDL cholesterol score.

11. A method according to claim 9, wherein the preventative health report card comprises obesity information comprising height, weight, and body mass index based on previous patient visit statistics.

12. A method according to claim 9, comprising:
   1) displaying on a single screen of the touch-screen display device:
      the preventative health measures that are upcoming for the patient;
      the preventative health measures that are overdue for the patient; and
      the preventative health report card for the patient; and
   2) permitting the patient to print out the displayed information on paper.

13. A method according to claim 1, wherein a plurality of kiosks are wirelessly connected to a server which accesses the at least one database.

* * * * *